United States Patent
Stolpe et al.

(10) Patent No.: US 7,291,294 B2
(45) Date of Patent: *Nov. 6, 2007

(54) IRIS ASSEMBLY FOR A PROSTHETIC EYE DEVICE

(75) Inventors: Carole Lewis Stolpe, 4239 Navajo St., Toluca Lake, CA (US) 91602; Frederick R. Lewis, deceased, late of Westlake Village, CA (US); by Frances C. Lewis, legal representative, Westlake Village, CA (US)

(73) Assignee: Carole Lewis Stolpe, Toluca Lake, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 11/206,336

(22) Filed: Aug. 18, 2005

(65) Prior Publication Data

US 2005/0275137 A1 Dec. 15, 2005

Related U.S. Application Data

(63) Continuation-in-part of application No. 10/192,958, filed on Jul. 11, 2002, now Pat. No. 7,029,608.

(51) Int. Cl.
*B29D 11/00* (2006.01)
(52) U.S. Cl. .......................... 264/1.7; 156/61
(58) Field of Classification Search ................ 264/1.1, 264/1.7, 1.32; 623/4.1, 6.64; 156/61
See application file for complete search history.

(56) References Cited

U.S. PATENT DOCUMENTS

| | | | | |
|---|---|---|---|---|
| 4,762,495 A | | 8/1988 | Maloney et al. | |
| 5,733,333 A | | 3/1998 | Sankey | |
| 5,863,363 A | * | 1/1999 | Sankey | 156/61 |
| 6,143,026 A | | 11/2000 | Meakem | |
| 6,391,230 B1 | * | 5/2002 | Sarbadhikari | 264/1.38 |
| 6,669,727 B1 | | 12/2003 | Young | |
| 6,746,120 B2 | | 6/2004 | Broderick et al. | |
| 6,811,461 B2 | | 11/2004 | Maddocks et al. | |
| 7,029,608 B1 | * | 4/2006 | Lewis et al. | 264/1.7 |

* cited by examiner

*Primary Examiner*—Suzette Gherbi
(74) *Attorney, Agent, or Firm*—Eley Law Firm Co.; James Eley; Michael Forhan

(57) ABSTRACT

An iris assembly for a prosthetic eye comprising a button having a frontside surface. An iris member is joined to the button frontside surface and has an iris image disposed thereon. The iris image is provided using digital image capture, storage, enhancement, and printing techniques, and is provided onto a suitable substrate. A cornea piece is made from a clear material, and is joined to the iris member frontside surface. Prior to joining, the iris member is encapsulated with a clear protective film thereover that operates to protect the iris image from unwanted smudging or other type of distortion during the step of joining the cornea piece. The iris assembly yields an accurate reproduction of the iris portion of a patient's natural eye in a manner that is both time efficient and cost effective.

23 Claims, 6 Drawing Sheets

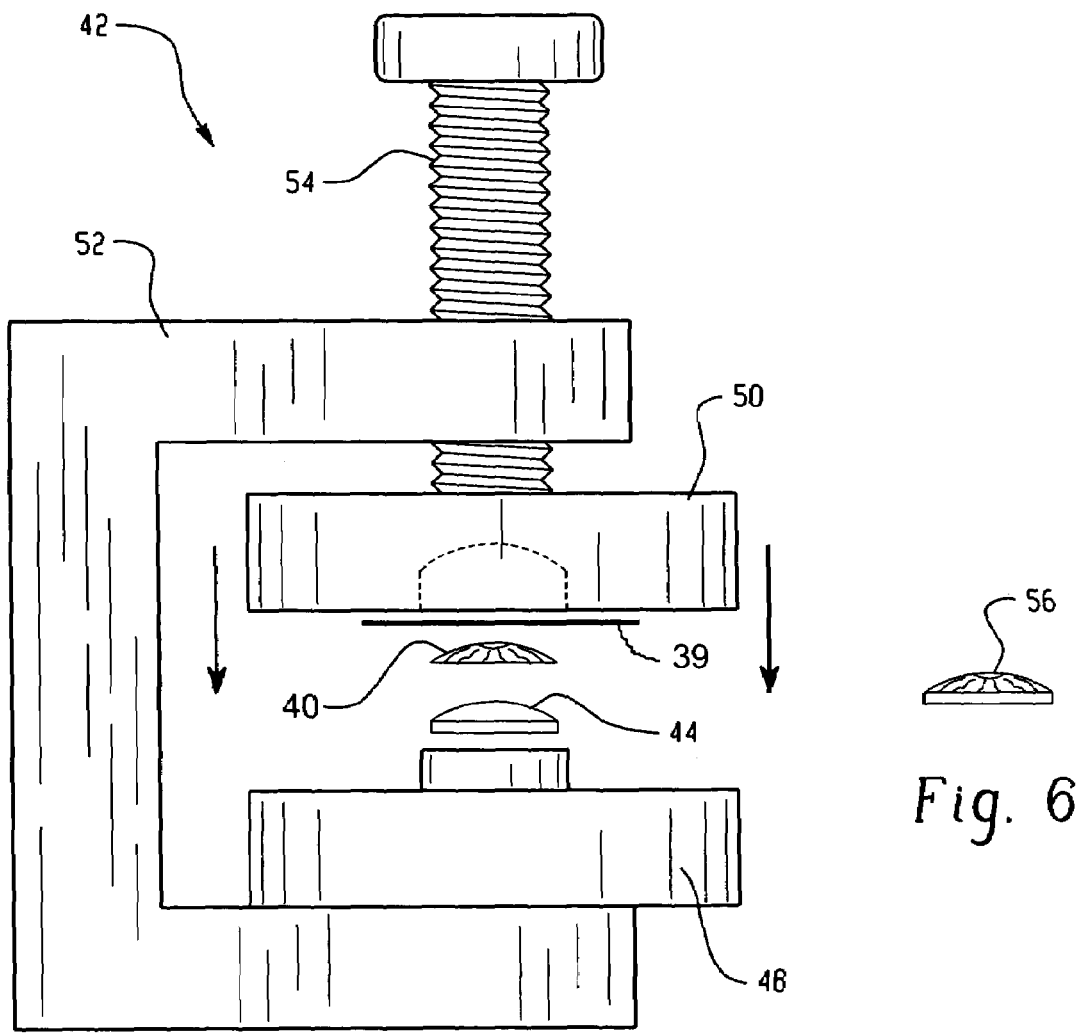
Fig. 5
Fig. 6
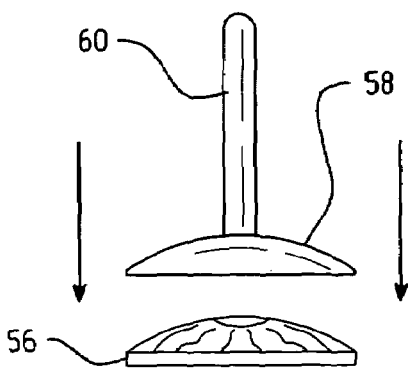
Fig. 7
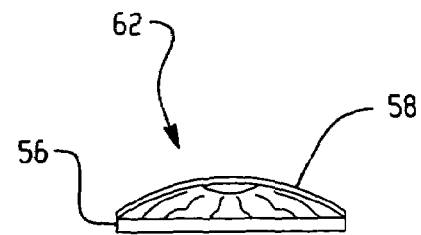
Fig. 8

IRIS ASSEMBLY FOR A PROSTHETIC EYE DEVICE

This application is a continuation-in-part of U.S. utility patent application Ser. No. 10/192,958, filed Jul. 11, 2002, now U.S. Pat. No. 7,029,608 the contents of which are hereby incorporated by reference.

FIELD

This invention relates to an iris assembly as used with a prosthetic eye device and, more particularly, to an iris assembly and method of making the same having a matching appearance of a natural eye in a manner that is both time and cost efficient.

BACKGROUND

Prosthetic eye devices are known in the art and can be configured to partially or completely replace an eye, e.g., a human eye for the aesthetic purpose of providing a more normal appearance. People can require use of such prosthetic eye device arising from a variety of reasons, such as an accident, disease or birth defect. Thus, the type of prosthetic eye device that is used can and will vary in its design depending on the particular application. In the case where the entire eye is being replaced, or a case where a frontside portion of the existing eye is being complemented, the prosthetic eye device can include an iris portion that is constructed to replicate the appearance of a natural eye, e.g., to replicate the appearance of the iris of the patient's existing eye. The iris portion of the device preferably comprises a complex colored and patterned portion that extends concentrically around the pupil portion of the eye to the sclera or white portion of the eye.

Prosthetic eye devices, e.g., in the form of a replacement or artificial eye, are conventionally made from materials such as methyl methacrylate and comprise an iris assembly positioned at a frontside portion of the eye device that is intended to replicate the color and patterning of a natural eye. The iris assembly is formed from a composite construction of individual elements. Typically, the iris image, depicting the complex color and patterning of the eye, is provided on a flat disk-shaped rigid plastic element.

The most difficult and time-consuming part of making a prosthetic eye device comprising an iris assembly is duplicating the iris of the patient's natural eye, as humans have a complex multicolored and patterned iris that can vary significantly from person to person. To achieve realistic color and pattern matching it has been the conventional practice to make the entire iris image by the time-consuming process of hand-painting the color and pattern of the iris in a manner matching the person's existing eye onto a piece of plastic by hand. In order to obtain the desired color intensity of the iris, oil-based paints are often used or mixed with acrylic paints.

An alternative method of replicating the iris portion of the eye for use in a prosthetic eye device involves a process of printing onto a flat sheet of photographic film or photographic paper a basic color of an iris. In this method, the basic color of an iris is printed by a conventional screen printing technique onto the flat piece of photographic film or paper as a starting point, then the film or paper is placed on a flat disk-shaped plastic element. The basic color is selected to generally match the underlying color of the patient's iris. The desired iris image matching the patient's eye, comprising the complex arrangement of coloring and patterning, is then provided by hand painting over the printed base color. This method was thought useful for potentially minimizing the amount of hand painting required during iris assembly formation by providing a basic colored foundation.

While the above-described photographic technique was helpful in reducing the amount of time necessary to create the iris image by reducing the amount of initial hand painting, this technique is not without its problems. For example, during subsequent steps in making the prosthetic eye device, the iris image can become distorted. This occurs because the subsequent processing steps involved in making a prosthetic eye device involves exposing the iris image to adhesives having strong solvents. The presence of these solvents is known to cause the image captured on photographic film or photographic paper to be dissolved or otherwise distorted.

There are known disadvantages to the above-described conventional methods of making the iris assembly for use in a prosthetic eye device. A first disadvantage relates to the current practice of placing the iris image onto a flat substrate, e.g., a disk-shaped plastic element, whether the iris image is created entirely by hand painting or by the hybrid process of hand painting over the printed base color. In either technique the iris image is flat and placed on a flat substrate. In many applications the prosthetic eye device is made to complement an existing portion of a patient's eye or ocular implant. This type of fitment often requires that a backside surface portion of the prosthetic eye device, e.g., a portion that includes a backside surface of the iris assembly, be configured having a nonplanar, e.g., a concave geometry. Conventional iris assemblies comprising an iris image placed on a flat or planar substrate are not well suited for this type of prosthetic eye device application because they do not permit surface shaping. Another disadvantage associated with conventional iris assemblies comprising a flat iris image is that, while appearing normal from a front-facing view, the iris image does not appear normal-looking from a side view.

Another known disadvantage associated with the above-described methods of making an iris assembly relates to the current practice of having to paint either the entire iris image, or a portion of the iris image, by hand. Since the color and pattern of a person's iris is unique and may be quite complex, the process of painting the entire iris image by hand involves a time-consuming practice of starting from scratch each time. The time spent in creating the desired iris image is reduced somewhat by using the screen printing technique. However, because the screen printing technique still involves some amount of hand painting, it is still time consuming. Additionally, in either technique, once the iris image is painted it may take many iterative steps of modifying the initial image to perfect the look of the iris in the completed iris assembly. Oftentimes it is less time consuming to start from scratch rather than to modify an existing image.

Another disadvantage relates to the current practice of using oil-based paints to provide the desired iris color intensity. It is known that the use of such oil-based paints have a coefficient of expansion that is different than that of the surrounding monomeric or polymeric materials that are used to form the remaining components of the iris assembly. Because a prosthetic eye device is exposed to moisture when worn and to repeated cycles of wetness and dryness, it is theorized that the different coefficients of expansion between the adjacent members in the iris assembly are responsible for delamination of such members, whereby the painted paper member becomes separated from adjacent iris assembly components. This delamination is not desirable as it makes the iris portion of the prosthetic eye appear cloudy or distorted, ultimately requiring replacement.

Another disadvantage also relates to the current practice of hand painting the iris image and using oil-based paints to provide the desired iris color and pattern onto the plastic element. During the process of making the iris assembly, after the iris image is painted on the plastic element, a clear lens cover or cornea piece is placed over and adhered to the painted surface of the plastic element using a suitable adhesive. During the step of adhering the front cover to the iris image plastic element it is sometimes necessary to move the front cover vis-à-vis the plastic element to provide a desired complementary fit. During this step it is known that the painted iris image can smear or otherwise become distorted, thus rendering the iris element useless and requiring that a new iris element be painted. As mentioned briefly above, this unwanted distortion of the iris image during attachment of the cornea piece of the assembly is also known to occur when using an iris image formed by photographic technique described above due to the interaction of solvents in the adhesive with the chemicals in the photographic film or photographic paper.

It is, therefore, desired that an iris assembly be constructed for use in a prosthetic eye device in a manner that increases the overall efficiency of making the iris assembly and the prosthetic eye device, e.g., a replacement eye. It is also desired that the iris assembly be constructed in a manner that: (1) enables use of the same in applications calling for a nonplanar fitment of a prosthetic eye device with an adjacent portion of a patient's eye or ocular implant; (2) provides a normal appearing iris from both front and side views; (3) minimizes or eliminates the potential for iris assembly delamination; (4) minimizes or eliminates the potential for unwanted distortion of the iris image during iris assembly construction; and (5) minimizes or eliminates the need to start from scratch when changing or modifying the iris image during iris assembly construction.

SUMMARY

An iris assembly for use with a prosthetic eye device constructed according to an embodiment of this invention comprises an iris button having a frontside surface. In a preferred embodiment, the iris button is configured having a nonplanar frontside surface. An iris member is joined to the frontside surface of the iris button and has an iris image disposed onto a frontside surface of the iris member. The iris member is preferably shaped to conform to the iris button and is bonded to the iris member using a chemical agent.

In a preferred embodiment the iris image is provided using digital image capture, enhancement, storage, and photo reproduction printing techniques and is generated using a suitable print medium and print substrate. In a preferred embodiment the iris image is provided by a photo reproduction process of depositing a print medium in the form of a desired ink or toner, e.g., a lightfast quality ink or toner, onto a print substrate in the form of a desired permanent paper, e.g., a high-quality, acid-free paper. Use of a paper print substrate is desired as it is malleable, thereby enabling the iris image to be configured to include multiple or variable curves without distortion. The ability to conform the iris image in this manner allows for precise custom fitting of the iris and posterior of a prosthetic eye device, comprising the same, to tissues in the patient's eye socket.

A cornea piece is made from a clear material and is joined to the iris member's frontside surface. In a preferred embodiment the cornea piece is joined to the iris member by using a desired adhesive solution and curing the same at conditions of elevated temperature and pressure. Prior to joining, the iris member is encapsulated with a protective layer to prevent unwanted smudging or other type of distortion of the iris image that can occur during the step of joining the cornea piece. In a preferred embodiment the iris member is encapsulated by a process of impregnating the iris member with a desired chemical agent and then allowing the chemical agent to cure, thereby forming the protective layer.

Iris assemblies of this invention are constructed in a manner that provide a more accurate reproduction of the iris image and is performed in a manner that is both time efficient and cost effective when compared to conventional iris assemblies and methods for making the same. Specifically, this invention enables the iris image, or sections or parts of the same, to be stored electronically and exactly, accurately and consistently reproduced at any time. This invention further enables portions of the iris image, or the entire iris image, to be changed, modified, altered or resized as necessary without having to start from scratch.

BRIEF DESCRIPTION OF THE DRAWINGS

Further features of the inventive embodiments will become apparent to those skilled in the art to which the embodiments relate from reading the specification and claims with reference to the accompanying drawings, in which:

FIG. 5 is a side elevational view of a pressing device use to combine the shaped iris image with an iris button according to principles of this invention;

FIG. 6 is a side elevational view of the assembled shaped iris image and iris button of FIG. 5;

FIG. 7 is a side elevational view of the assembled shaped iris image and iris button of FIG. 6 as combined with a cornea;

FIG. 8 is a side elevational view of the assembled iris image, iris button, and cornea, forming the iris assembly of this invention;

DETAILED DESCRIPTION

Figure 1:
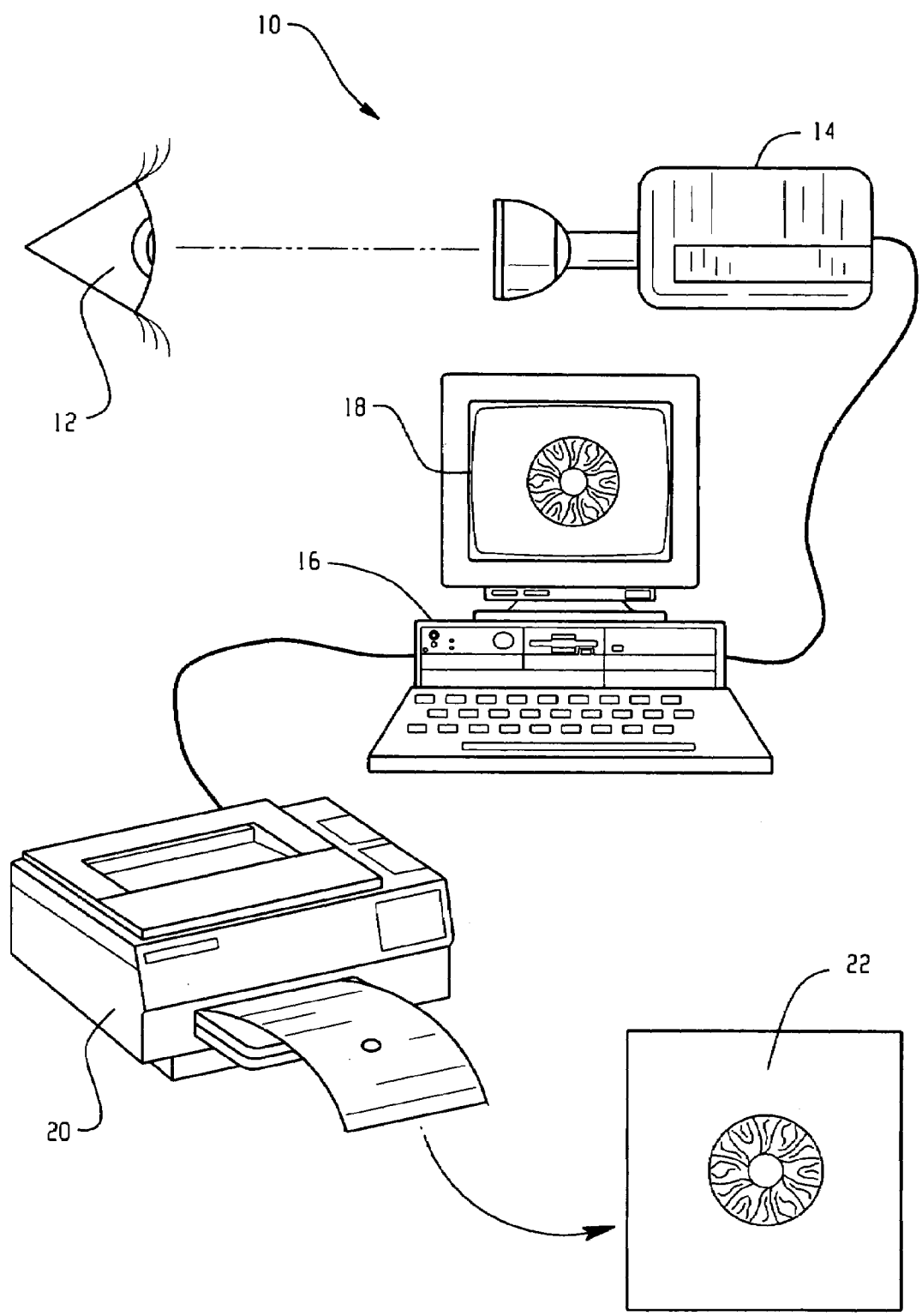
FIG. 1 is a schematic view of a system for forming an iris image used in constructing an iris assembly according to principles of this invention.

In the discussion that follows, like reference numerals are used to represent elements of like structure and function.

Iris assemblies of this invention are constructed using a digital image, digital image enhancement, digital image storage, and digital photo reproduction printing techniques to create an iris image matching the appearance of a natural eye. The iris image of this invention is provided in the form of a paper portion that is specially curved and processed to prevent unwanted distortion of the iris image during further assembly steps to form an iris assembly in a manner that is both time and cost effective when compared to conventional techniques. Iris assemblies of this invention can be used with a variety of different types of prosthetic eye devices calling for a replacement iris component. Such prosthetic eye devices can be used to partially compliment or completely replace a patient's eye.

FIG. 1 illustrates a system 10 and its basic components, according to principles of this invention, for capturing and replicating an iris image of a patient's eye. The system 10 involves the use of digital technology for this purpose. A desired iris image of a patient's eye 12 is captured using a digital camera 14. Digital cameras useful for this purpose include those configured to provide either a still or video capture of the eye and, more specifically, of the iris portion of the eye. Additionally, it is desired that the digital camera be equipped to download or transfer the digital image to a signal processor, such as a computer. An example digital camera useful for this task is one made by Sony identified as Mavica-MVC-FD95.

The digital camera is used to capture the iris image, comprising the iris color and pattern of the patient's eye. The digitally-captured image is downloaded by suitable cables or other transfer means known in the art to a signal processor 16 capable of receiving the digital image and storing it in a memory portion. In an example embodiment, the signal processor 16 is provided in the form of a computer that processes the electronic signals provided by the camera 14. An example computer useful for this task is one made by Dell and identified as a Precision Workstation 220.

The computer 16 is configured to include digital image software for reproduction and enhancement (not shown) that enables the computer to receive the digital image from the camera and present the same onto a suitable viewing means 18, such as a video monitor, thereby enabling one to view the results provided by the camera and/or computer. Suitable video monitors useful for this system include those conventional color computer monitors that are capable of providing a high resolution graphic image.

Example digital image software include those capable of enabling the computer to receive the image captured by the camera, transmit the captured image to the video monitor 18, and work or adjust/enhance the image to make desired changes to the color, pattern, size, and/or shape of the iris image as may be needed for the purpose of providing an iris image that matches the appearance of the patient's eye when provided in the finished iris assembly. The digital image software also includes the ability to store the captured and worked iris image, and transmit the iris image to a suitable printer for reproduction. Suitable digital image software for this purpose include Photoshop sold by Adobe, and Corel Draw and Corel Photostyler.

Once a desired iris image is obtained on the computer 16, the iris image is sent to a suitable photo reproduction means 20, such as a printer. The printer is a color printer that can work on ink or laser technology and is capable of providing a threshold resolution image 22 that can capture the complex color and pattern image of the iris. It is further desired that the printer be one capable of providing the iris image using a print medium and print substrate that does not present problems such as smudging and distorting during subsequent processing of the printed iris image.

It has been discovered through much experimentation that the choice of print medium, e.g., ink or toner, and the choice of print substrate, e.g., paper, that is used to capture the iris image 22 is important for helping to provide a stable, distortion resistant iris image. It is desired that the type of print medium used be one that is capable of providing a printed image having properties of extended lightfastness and improved stability, when compared to ordinary print inks or toners. In an example embodiment, the print medium is provided in the form of an ink, such as a dye ink, or a pigment ink, and the like. In a preferred embodiment, the print medium is provided in the form of a high-lightfastness color pigment ink referred to in the industry as "archival" ink.

It is desired that the type of print substrate used be one that is capable of providing properties of lightfastness and improved stability, when compared to conventional printing paper. It is also desired that the print substrate be formed from a material that permits the iris image to be shaped into a desired nonplanar configuration. In a preferred embodiment, the print substrate is provided in the form of an acid-free paper referred to in the industry as "archival" paper. It is further preferred that the paper have a flat matte surface.

Archival papers and inks are intentionally created for the purpose of providing enhanced photo reproduction image life, without unwanted fading, or distortion, on the order of 200 years. It has been discovered that the use of such ink and paper produces a printed iris image 22 that provides a level of image stability and resistance to fading, smudging, and distorting that exceeds that obtained by using conventional, i.e., nonarchival, ink and paper. In a preferred embodiment, the type of printer that is used to provide the iris image, using such archival ink and paper, is one manufactured by Epson as model number 2000P.

Using the above-described system 10, once an image of the patient's iris is taken and downloaded into the computer, it may or may not need working before being sent to the printer. Much depends on the capabilities of the camera, software, computer, and printer on whether the iris image as captured by the camera, processed by the computer, and printed by the printer will provide an iris image in the finished iris assembly that closely replicates the patient's natural iris. Therefore, it may be necessary that the iris image be worked or adjusted on the computer to make up for these potential shortcomings.

Additionally, in constructing the iris assembly of this invention, the iris image is ultimately placed behind a clear lens or cornea piece, which is also known to affect the final iris image. For example, while the printed iris image may look identical to the patient's actual iris, the printed iris image may look different, e.g., darker or lighter, from the patient's natural iris once the lens is placed over the iris image and the iris assembly is completed. Thus, the iris image can be worked, e.g., lightened or darkened, on the computer to anticipate this effect.

Once the desired iris image is printed, it may be desired to ensure that the ink used to print the iris image is fully dried or cured. In an example embodiment, the printed iris image is heat dried for a period of time. In an example embodiment, the iris image is heat dried for a period of about 30 minutes under a 100 Watt incandescent lamp. The step of heat drying operates to cure the ink in the printed image for the purpose of avoiding or preventing any unwanted smudging or distorting of the iris image during subsequent handling and/or processing.

Figures 2, 3, 4:
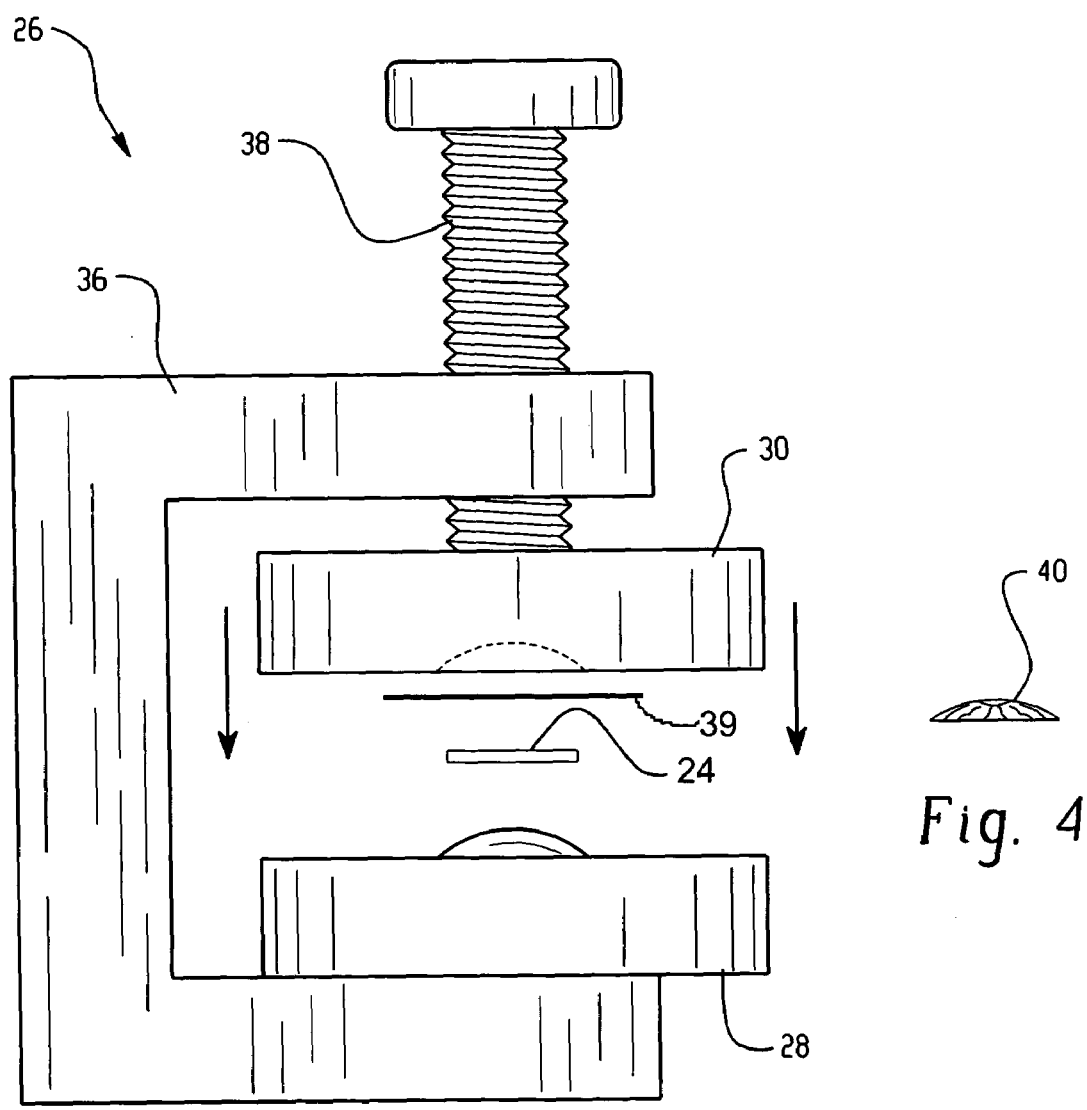
FIG. 2 is a schematic view of the iris image from FIG. 1 after it has been trimmed from the print substrate.
FIG. 3 is a side elevational view of a pressing device used to shape the iris image of FIG. 2 according to principles of this invention.
FIG. 4 is a side elevational view of the iris image after it has been shaped.

Once the iris image is captured, adjusted, printed, and dried according to the above-described system 10, it is trimmed. FIG. 2 illustrates the printed iris image of this invention after it has been trimmed along the outside border of the iris to form an iris member 24. The iris member 24 preferably comprises only the iris and pupil portions of the eye for the purpose of facilitating subsequent processing of the iris member. Because iris assemblies of this invention are being used directly to form a prosthetic eye device, the size of the iris member 24 is to scale.

Because the human iris has a nonplanar geometry, it is desired that the iris member 24 be shaped in a manner that replicates the patient's eye, thereby, providing an iris member that accurately replicates the natural appearance of a patient's eye. It is also desired that the iris member be shaped to have a nonplanar geometry for the purpose of configuring the iris assembly of this invention to permit proper fitment, of a prosthetic eye device comprising the same, with an adjacent portion of a patient's existing eye or ocular implant. A shaped iris member enables multiple curving of a backside surface of the iris assembly for providing precise custom fitting of the iris and posterior portion of a prosthetic eye to tissues in a patient's eye socket.

FIG. 3 illustrates a pressing means 26 useful for shaping the iris member 24 of this invention. The pressing means can be of any form, e.g., a clamp, press, or the like, that is capable of imposing a desired shape onto the iris member. In an example embodiment, the pressing means 26 is in the form of a two-piece press assembly comprising opposed first and second members 28 and 30, each having complementary surface features configured to correspond and register with one another.

Because the iris portion of the human eye generally has a convex shaped geometry, i. e., one defined having a radiused surface curvature, the surface features of the pressing means are configured to impose a convex shape onto the iris member 24 that is interposed therebetween. The pressing means 26 may include means for combining the first and second members together, or may be loaded into such means, e.g., in the form of a clamp 36 or the like. In an example embodiment, the first and second members 28 and 30 are loaded into the clamp 36, and a threaded clamp member 38 is turned to impose a desired pressure force between the members and onto the iris member 24. For purposes of protecting the iris image from any possible damage during this process, a protective element 39 such as a piece of plastic film, foil or the like can be used to isolate the printed surface of the iris member 24 from the second member 30. FIG. 4 illustrates an iris member 40 of this invention after it has been shaped by the above-described process. A feature of this invention is that the iris member 40 does not become significantly creased or suffer any other type of significant surface distortion during the shaping process. This is thought to be due to the use of the archival paper. Another feature of this invention is that the iris image does not become smudged or distorted during the pressing process. This is thought to be due to the use of the archival paper in combination with the archival ink, and dry heat curing of the same.

After the iris member 40 is shaped, it is treated for the purpose of further protecting the iris image from being smudged or otherwise distorted during subsequent handling and/or processing. In an example embodiment, the shaped iris member 40 is covered or encapsulated with a protective layer of clear material. This can be done, for example by using a preformed film or by soaking the iris member in a chemical solution and allowing the solution to cure and, thereby form the protective layer. In a preferred embodiment, the iris member 40 is soaked with a chemical solution for a sufficient period time to impregnate the iris member with the solution. The chemical solution can be one that is chemically compatible with the materials of the iris member, and with the materials of the other contacting portions of the iris assembly, and one capable of curing to provide a crosslinked protective covering over the iris member 40. In a preferred embodiment, the chemical solution is a mixture of methyl methacrylic monomer and polymer that is provided in the form of a syrup-like viscous liquid.

In a preferred embodiment, the iris member 40 is soaked in the chemical solution for a period of approximately one hour. After soaking, the iris member 40 is heat dried for a period of time at a curing temperature, e.g., for methyl methacrylic at about 212° F. In a preferred embodiment, this curing process takes place for period of approximately one hour under a 100 Watt incandescent lamp. During the step of heat drying, it is theorized that the chemical solution undergoes chemical crosslinking reactions that operate to encapsulate the iris member 40 and the iris image thereon, forming a clear protective covering thereover. It has been discovered through much experimentation that this step of impregnating and encapsulating the iris member is critical in protecting the iris image and, thereby preventing smudging or distorting of the iris image during subsequent processing to construct the iris assembly. Impregnation and encapsulation of the iris member 40 also eliminates the possibility of future delamination, e.g., between the iris member and a cornea piece, that can allow in light from the side posterior of the iris assembly and cause the iris image to appear distorted.

After the iris member is encapsulated, it is mounted to an iris button. FIG. 5 illustrates a pressing means 42 useful for combining an iris button 44 to a backside surface of the iris member 40. The iris button 44 is formed from a suitable rigid material, such as plastic or the like. In a preferred embodiment, the iris button 44 is formed from the same type of material that is used to form the remaining portion of the prosthetic eye device, e.g., methyl methacrylate. The iris button 44 has a frontside surface that is shaped to complement the backside surface of the iris member 40, e.g., that is convex shaped. The iris button 44 is sized having a diameter that is approximately that of the iris member.

In an example embodiment, the pressing means 42 can be similar to that used for the shaping step, e.g., a two-piece press assembly comprising first and second members 48 and 50. The first press assembly member 48 is configured to cooperate with a backside surface of the iris button 44, and the second press member 50 is configured to cooperate with a frontside surface of the iris member 40. In an example embodiment the first and second members 48 and 50 are loaded into a clamp 52 having a threaded member 54 that is turned to impose a desired pressure force between the two members, thereby pressing the iris button and iris member together. For purposes of protecting the iris member 40 from any possible damage during this process, a protective element 39 such as a piece of plastic film, foil or the like can be used to isolate the iris member from the second member 50.

Prior to loading the iris member 40 and iris button 44 into the pressing means 42, an adhesive solution is placed between the adjoining surfaces of the iris member and iris button. The type of adhesive solutions useful for joining the iris member and iris button together include those having chemistries that complement the materials of, and that are capable of forming a bond between, the iris member and iris button. In an example embodiment, the adhesive solution that is used is the same as that used to encapsulate the iris member, i.e., a mixture of methacrylic monomer and polymer that is provided in the form of a syrup-like viscous liquid.

The desired adhesive solution is applied both to the backside surface of the iris member and the frontside surface of the iris button. Once the adhesive solution has been applied, the iris member and iris button are placed together and are loaded into the pressing means 42. The clamp is operated to press the two press members 48, 50, and the iris member 40 and iris button 44, together. The clamp 52 and press means 48, 50 are then exposed to an elevated temperature for the purpose of causing the adhesive solution to undergo chemical reaction to thereby bond the iris member and iris button together.

It has been discovered through much experimentation that successful bonding of the iris member 40 and iris button 44 is achieved under conditions of elevated temperature and, more specifically, under conditions of dry heat. In a preferred embodiment, where the adhesive solution is the methyl methacrylic monomer and polymer mixture described above, the clamp and press means is exposed to a pressure of about 25 PSI and a dry heat temperature in the range of from between 195 to 215° F., for a period of approximately 20-30 minutes. After this period of time, the clamp and pressing means are removed from the heat and allowed to cool. FIG. 6 illustrates the bonded together iris subassembly 56, comprising the iris member 40 and iris button 44. After removal from the press means, the iris subassembly 56 is cleaned by appropriate means to remove any unwanted adhesive that may have run onto the backside surface of the iris button.

FIG. 7 illustrates the process of joining a cornea piece 58 to the iris subassembly 56. The cornea piece 58 is in the form of a clear plastic member that is configured to fit over the frontside or iris image of the iris subassembly 56, e.g., that has an adjoining concave surface. Suitable plastics useful for forming the cornea piece 58 include those that are chemically compatible with both the iris subassembly, and the remaining portion of the prosthetic eye device. In an example embodiment, the cornea piece 58 is formed from methyl methacrylate. In the embodiment illustrated in FIG. 7, the cornea piece 58 has a projecting stem 60 that is provided for the purpose of facilitating handling of the completed iris assembly in forming the prosthetic eye device, which stem is eventually removed.

Prior to combining the two pieces, an adhesive solution is placed between the adjoining surfaces of the iris subassembly 56 and the cornea piece 58. The type of adhesive solution useful for joining the iris subassembly and cornea piece together include those having chemistries that complement the materials of, and that are capable of, forming a bond between, the two members. In an example embodiment, the adhesive solution that is used is the same as that used to encapsulate the iris member, i.e., a mixture of methyl methacrylic monomer and polymer that is provided in the form of a viscous syrup-like liquid.

The desired adhesive solution is applied both to the backside surface of the cornea piece 58 and the frontside surface or iris image of the iris subassembly 56. Once the adhesive solution has been applied, the iris subassembly and the cornea piece are pressed together by hand pressure. Any adhesive solution that runs out from the two combined members, and onto the cornea piece, is cleaned away. The combined iris subassembly and cornea piece is then exposed to an elevated temperature and pressure for the purpose of causing the adhesive solution to undergo chemical reaction to bond the iris subassembly and cornea piece together and, thereby form the completed iris assembly 62 illustrated in FIG. 8. During this process it is important that a sufficient quantity of the adhesive solution be applied to the joined together members 56, 58 so that a small quantity of the adhesive slips out between the two pieces to form a seal along the common periphery.

It has been discovered through much experimentation that successful bonding is achieved under conditions of pressure and elevated temperature and, more specifically, under conditions of dry heat. In a preferred embodiment, where the adhesive solution is the methyl methacrylic monomer and polymer mixture described above, the combined iris subassembly and cornea piece is exposed to pressure of about 25 PSI and a dry heat temperature in the range of from between 195 to 215° F., for a period of approximately 20-30 minutes. After this period of time, the newly-formed iris assembly 62 is removed from the heat and allowed to cool.

The iris assembly is next cleaned using appropriate means, for the purpose or removing any excess adhesive solution that may have run onto nonjoined surfaces of the combined members, and polished using appropriate means. The resulting iris assembly is then ready for combining with the other portions of the prosthetic eye device to form the finished product.

Key features of this invention include, but are not limited to: (1) the use of digital image capture, enhancement, storage, and photo replication technologies to produce an iris image, thereby improving reproduction accuracy and saving time and cost when compared to the conventional method of partially or entirely hand painting the iris image; (2) the use of a conformable and print receptive substrate for capturing the iris image, and the subsequent curing of the printed image, to provide an iris image that is resistant to smudging and/or distortion during subsequent handling or processing; (3) the use of a chemical agent to impregnate and encapsulate the iris image after it has been printed, thereby forming a protective cover or film over the iris image to protect the iris image and further prevent smudging or distorting of the image during subsequent processing; (4) the use of a nonplanar iris member for the purpose of both accurately replicating the geometry of a human iris, and enabling precise fitment of a prosthetic eye device comprising the same; and (5) the use of a special chemical agent in adhering the iris member to the iris button, and adhering the iris subassembly to the cornea lens, and the use of elevated pressure and dry heat to perfect bonding of the same.

Figure 9:
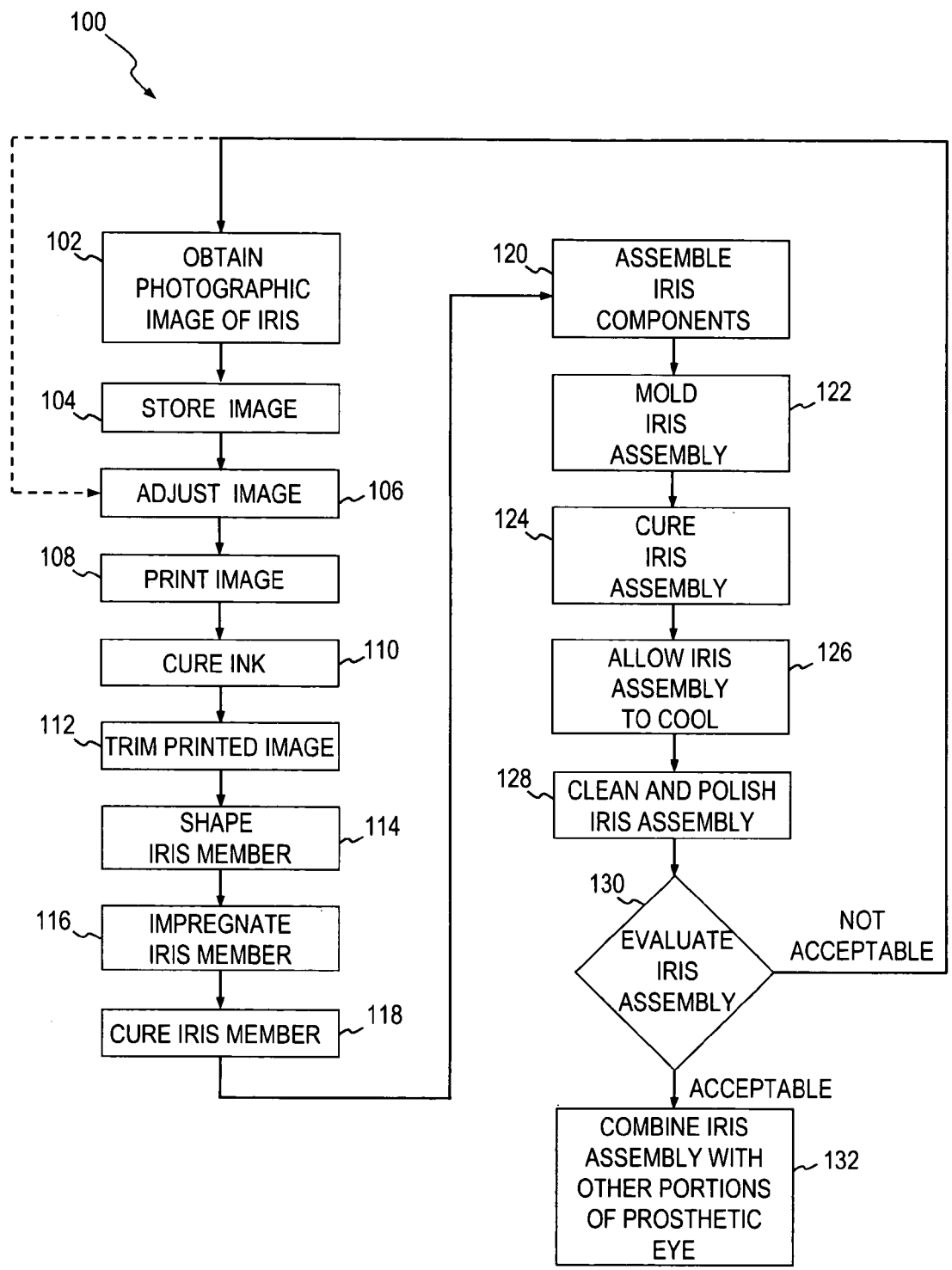
FIG. 9 is a flow diagram of a method for making an iris assembly for a prosthetic eye device according to another embodiment of the present invention.
Figure 10:
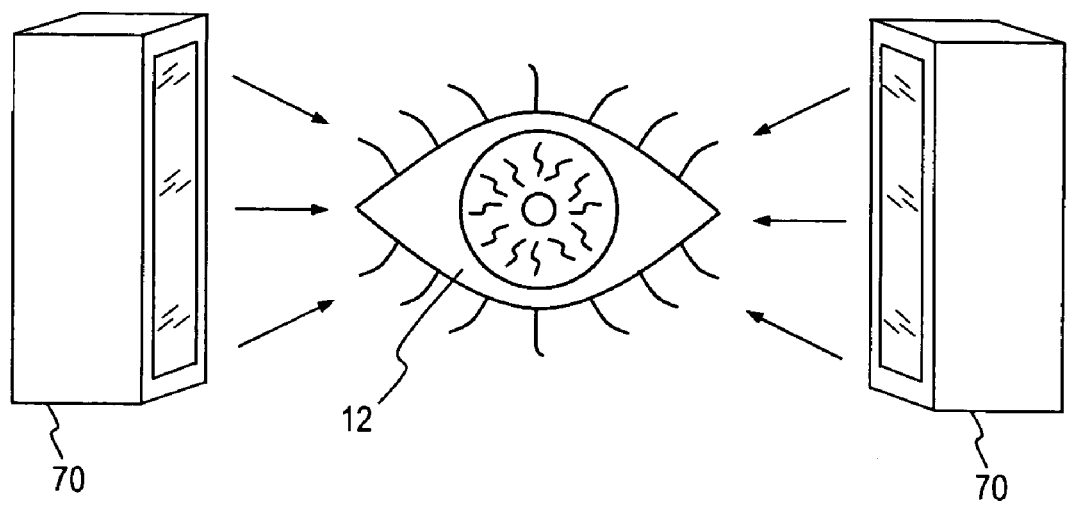
FIG. 10 depicts a lighting system usable with the system of FIG. 1.

A process 100 for producing an iris assembly for a prosthetic eye is shown in FIG. 9 according to an alternate embodiment of the present invention. In this embodiment a photographic image, made of a patient's natural eye 12, is obtained at step 102 using system 10 of FIG. 1 and associated steps. The image is preferably of high magnification and high resolution in order to facilitate later adjustment and enhancement, as will be described below. Camera 14 may optionally include a lighting arrangement comprising two or more conventional flash elements 70, as shown in FIG. 10. Flash elements 70 are spaced apart and are aimed toward the patient's natural eye 12 such that the eye is positioned generally intermediate the flash elements. This provides substantially even lighting for obtaining an image having good color reproduction, capturing details of the texture and patterns of the iris, and minimizing shadowing and flash effects.

At step 104 the iris image is stored for later use. In a preferred embodiment the image is obtained with a digital camera 14 and stored as a digital data file in a memory portion of a signal processor 16, such as a computer, in the manner previously described. It is important to note that the image obtained from camera 14, although having high resolution and high magnification, may be unsuitable for use in a prosthetic device due to various factors. For example, refraction of light passing through the cornea can shift the color slightly and de-emphasize iris patterns, with the result that the prosthetic eye does not satisfactorily match the natural eye. At step 106 the color, texture and patterns of the stored image are adjusted by various techniques including, without limitation, using the previously-discussed digital image software to shift the color of portions of the image, add splashes of color, add one or more layers of colors having varying transparency, reproportion and/or re-size the image or features thereon, and emphasize lines and details. The resulting adjusted image often appears somewhat exaggerated and is often significantly different from the natural eye when viewed on monitor 18 or in printed form 22; however, the adjusted iris image closely matches the natural eye after it is joined with the cornea. Step 106 requires an artistic approach and is part of an iterative process, as will be seen more clearly below.

At step 108 the adjusted image is printed on a photo reproduction means 20, in the manner previously described, using the print substrate and inks likewise previously described. In a preferred embodiment, archival inks and paper are used. Once the iris image 22 is printed (FIG. 1), it is cured at step 110 to ensure that the ink used to print the image is fully dried. In an example embodiment, the printed iris image 22 is heat dried for a period of time, such as for about 30 minutes under a 100 Watt incandescent lamp. The step of heat drying is to prevent smudging or distortion of the iris image 22 during subsequent handling and/or processing.

At step 112 the iris image is trimmed in the manner previously described. FIG. 2 illustrates the printed iris image of this invention after it has been trimmed along the outside border of the iris to form an iris member 24 (FIG. 2). The iris member 24 preferably comprises only the iris and pupil portions of the eye for the purpose of facilitating subsequent processing of the iris member. Because iris assemblies of this invention are being used directly to form a prosthetic eye device, the size of the iris member is to scale.

As previously noted, it is desirable to shape the iris member 24 to accurately replicate the natural appearance of a patient's eye and to permit proper fitment of a prosthetic eye device comprising the same. Accordingly, the trimmed member 24 is shaped at step 114 in the manner previously described, using the pressing means of FIG. 3 to form a convex-shaped iris member 40 (FIG. 4).

At step 116 the iris member 40 is soaked in a chemical solution that impregnates, encapsulates and substantially plasticizes the iris member, thereby forming a protective layer. The chemical solution can be one that is chemically compatible with the materials of the iris member 40, and with the materials of the other contacting portions of the iris assembly, and one capable of curing to provide a crosslinked protective covering over the iris member. In a preferred embodiment the iris member 40 is soaked for about an hour in chemical solution that is a mixture of methyl methacrylic monomer and polymer provided in the form of a syrup-like viscous liquid.

After soaking the iris member 40 in the chemical solution of step 116 it is cured by heat drying at step 118 for a period of time at a curing temperature, e.g., for methyl methacrylic at about 212° F. In a preferred embodiment this curing process takes place for period of approximately one hour under a 100 Watt incandescent lamp.

Figure 11:
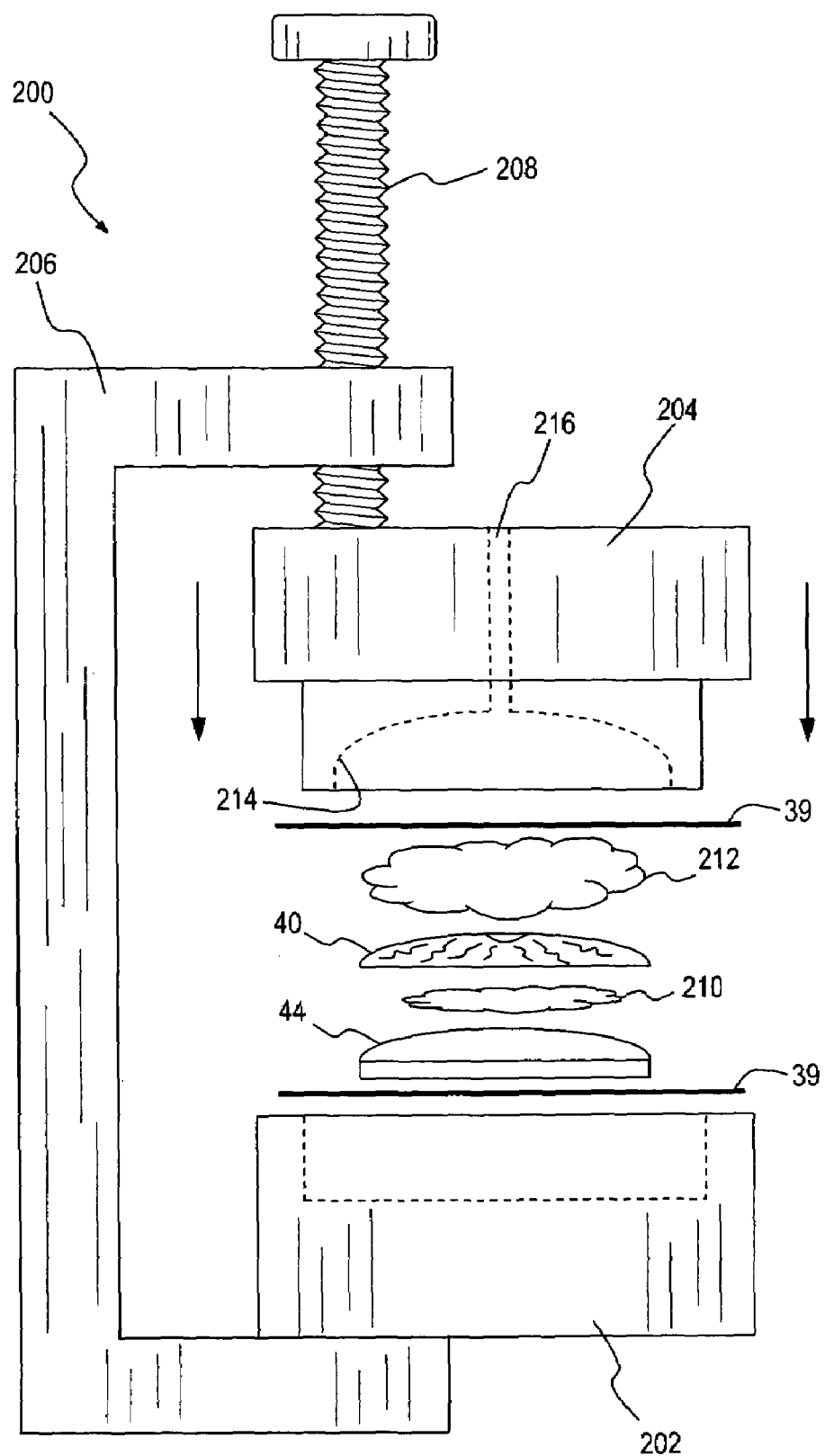
FIG. 11 is a side elevational view of a pressing device for molding a cornea to an iris member and an iris button according to an alternate embodiment of the present invention.

With reference to FIGS. 9 and 11, after the iris member 40 is encapsulated it is assembled with an iris button 44 at step 120. As previously noted, iris button 44 is formed from a suitable rigid material, such as plastic or the like. In a preferred embodiment, the iris button 44 is formed from the same type of material that is used to form the remaining portion of the prosthetic eye device, e.g., methyl methacrylate. The iris button 44 has a frontside surface that is shaped to complement the backside surface of the iris member 40, e.g., that is convex shaped. The iris button 44 is sized having a diameter that is approximately that of the iris member 40.

A pressing means 200 may be used to combine a backside of iris member 40 to a frontside surface of iris button 44 and to form a cornea portion, all in a single step. Pressing means 200 may be a two-piece press assembly and may comprise first and second members 202 and 204. The first press assembly member 202 is configured to cooperate with a backside surface of the iris button 44, and the second press member 204 is configured to cooperate with a frontside surface of the iris member 40. In an example embodiment, the first and second members 202 and 204 are loaded into a clamp 206 having a threaded member 208 that is turned to impose a desired pressure force between the two members, thereby pressing the iris member 40 and iris button 44 together.

At step 120, prior to loading the iris member 40 and iris button 44 into the pressing means 200, an adhesive solution 210 is placed between the adjoining surfaces of the iris member and iris button. The type of adhesive solutions useful for joining the iris member and iris button together include those having chemistries that complement the materials of, and that are capable of forming a bond between, the iris member and iris button. In an example embodiment, the adhesive solution 210 that is used is the same as that used to encapsulate the iris member, i.e., a mixture of methacrylic monomer and polymer that is provided in the form of a syrup-like viscous liquid. Adhesive solution 210 is applied to either or both the backside surface of the iris member 40 and the frontside surface of the iris button 44.

A cornea piece in the form of a clear plastic member is molded to fit over the frontside of iris member 40. Suitable plastics useful for forming the cornea piece includes those that are chemically compatible with both the iris subassembly and the remaining portion of the prosthetic eye device. In an example embodiment, at step 120 a mixture of methacrylic monomer and polymer is provided in the form of a malleable cornea molding material 212 having the consistency of modeling clay. Cornea molding material 212 is placed between the frontside of iris member 40 and second press member 204. A protective element 39 such as a piece of plastic film, foil or the like may be placed between the assembled components of step 120 and either or both of press members 202, 204, for the purpose of protecting the components from damage.

At step 122 a clamp 206 is operated by turning a threaded member 208 to press the two press members 202, 204 and, in turn, the iris button 40, iris member 46 and cornea molding material 212 together. The resulting pressure causes cornea molding material 212 to conform to a concave shape, the shape being controlled by a forming surface 214 of second press member 204. The amount of cornea molding material 212 is preferably sufficient to extrude a portion of the cornea molding material into a stem-forming aperture 216, filling the aperture with the molding material. A stem portion 224 (FIG. 12) projecting from the cornea piece is thus formed that is useful for handling the completed assembly 220 during subsequent processing.

At step 124 the clamp 206 and press means 202, 204 containing the iris assembly are exposed to an elevated temperature and pressure for the purpose of curing by causing the adhesive solution and molding material to undergo chemical reaction to thereby mold the cornea piece to the iris member and bond the iris member and iris button together. During this process it is preferable that a sufficient quantity of the adhesive solution 210 be applied to the joined-together members 40, 44 so that a small quantity of the adhesive exudes from between the two pieces to form a seal along the common periphery between the iris member 40 and the iris button 44. It is likewise preferable that the cornea molding material 212 contacts the adhesive solution 210 along the common periphery, so as to further form a seal between the cornea portion and the frontside of iris member 40.

It has been discovered through much experimentation that successful curing is achieved under conditions of elevated temperature and, more specifically, under conditions of steam and pressure. An example device useful for heating and pressurizing is an ERKODENT LIQUISTEAM-E polymerization apparatus. In a preferred embodiment, where the adhesive solution 210 and cornea molding material 212 is the methyl methacrylic monomer and polymer mixture described above, the clamp and press means is exposed to a pressurized steam heat having temperature of about 205-225° F. at a pressure of about 3-7 bar, for a period of approximately 20-30 minutes. After this period of time a newly-formed iris assembly 220 (FIG. 12) is removed from the heat and allowed to cool, as at step 126.

Figure 12:
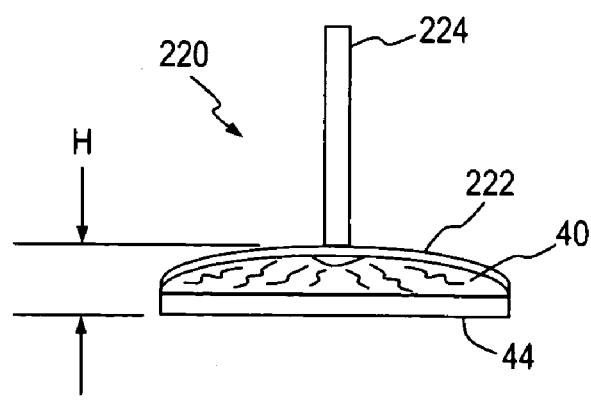
FIG. 12 is a side elevational view of an iris assembly according to an alternate embodiment of the present invention.

As can be seen from FIG. 12, iris assembly 220 comprises iris member 40, button 44, and a molded cornea portion 222. Cornea portion 222 further comprises a molded projecting stem portion 224 for the purpose of facilitating handling of the completed iris assembly in forming the prosthetic eye device, which stem is eventually removed.

With reference to FIGS. 9 and 12, after iris assembly 220 has cooled it is removed from the press means 200 and cleaned at step 128 by appropriate means to remove any unwanted adhesive and/or flash resulting from adhesive 210 and molding material 212. In one embodiment molded stem portion 224 is chucked to a conventional rotating device, such as a drill or lathe. Iris assembly 220 is then rotated and the unwanted material removed from the iris assembly with a stationary knife blade that is manually or automatically moved proximate the iris assembly. The knife blade may also be used to trim the cornea piece to a desired size and shape, for example, a height "H" of about 4.2 mm. A conventional polishing cloth or brush may then be used while spinning the iris assembly 220 to polish the molded cornea portion 222 for clarity. Iris assembly is then removed from the rotating device and stem 224 is removed.

The resulting iris assembly 220 is visually evaluated at step 130 to determine whether it sufficiently matches the patient's natural eye. If the match is acceptable, iris assembly 220 is combined at step 132 with the other portions of the prosthetic eye device in any manner now known or hereafter invented to form the finished product. However, if iris assembly 220 does not sufficiently match the patient's natural eye, depending upon the type and degree of disparity either the stored image of step 104 is adjusted again at step 106 or a new image is obtained at step 102, with the corresponding subsequent steps of process 100 being followed until an acceptable iris assembly 220 results at step 130.

While this invention has been shown and described with respect to a detailed embodiment thereof, it will be understood by those skilled in the art that changes in form and detail thereof may be made without departing from the scope of the claims of the invention. Accordingly, it is to be understood that within the scope of the appended claims, iris assemblies of this invention may be embodied other than as specifically described herein.

What is claimed is:

1. A method for making an iris assembly for a prosthetic eye device, comprising the steps of:
   obtaining a photographic image of an iris portion of a natural eye;
   storing the photographic image;
   adjusting the stored photographic image such that the image replicates the iris portion of the natural eye;
   printing the adjusted photographic image;
   curing the printed photographic image;
   trimming the cured photographic image to form an iris member;
   shaping the trimmed iris member;
   impregnating the shaped iris member with an adhesive solution;
   curing the impregnated iris member;
   assembling together a backside surface of the cured iris member to a frontside surface of an iris button with an adhesive solution therebetween, and placing a cornea molding material proximate a frontside surface of the cured iris member;
   molding together the cured iris member, iris button and cornea molding material to form a molded iris assembly;
   curing the molded iris assembly;
   allowing the cured iris assembly to cool; and
   cleaning and polishing the cooled iris assembly, wherein the cleaned and polished iris assembly yields an accurate reproduction of the iris portion of the natural eye.

2. The method of claim 1 wherein the photographic image is obtained with a digital camera.

3. The method of claim 2, further comprising the step of obtaining the photographic image using a plurality of flash elements to provide even lighting of the natural eye.

4. The method of claim 1 wherein the obtained photographic image is stored in a memory portion of a computer.

5. The method of claim 1 wherein the stored photographic image is adjusted with digital image software by at least one of shifting the color of portions of the image, adding splashes of color, adding one or more layers of colors having varying transparency, reproportioning the image, re-sizing the image or features thereof, and emphasizing lines and details of the image.

6. The method of claim 1 wherein the adjusted image is printed upon archival paper.

7. The method of claim 6 wherein the adjusted image is printed with archival ink.

8. The method of claim 1 wherein the printed image is cured by placing it under an incandescent lamp for a predetermined period of time.

9. The method of claim 1 wherein the trimmed iris member is formed in a convex shape.

10. The method of claim 1 wherein the shaped iris member is impregnated with an adhesive solution comprising a mixture of methyl methacrylic monomer and polymer having a syrup-like viscosity.

11. The method of claim 1 wherein the impregnated iris member is cured by placing it under an incandescent lamp for a predetermined period of time.

12. The method of claim 1 wherein the cornea molding material is a malleable mixture of methacrylic monomer and polymer having the consistency of modeling clay.

13. The method of claim 1 wherein the molded iris assembly is cured under conditions of steam and high pressure for a predetermined period of time.

14. The method of claim 13 wherein the molded iris assembly is cured under a pressurized steam heat having a temperature of about 205-225° F. at a pressure of about 3-7 bar, for a period of approximately 20-30 minutes.

15. The method of claim 1, further comprising the step of molding a projecting stem portion of the molded iris assembly.

16. The method of claim 15, further comprising the steps of rotating the cooled iris assembly about the projecting stem portion to clean and polish the cooled iris assembly, then removing the projecting stem portion from the cleaned and polished iris assembly.

17. The method of claim 1, further comprising the step of visually evaluating the cleaned and polished iris assembly and combining it with other components to form a prosthetic eye if it is acceptable.

18. The method of claim 1, further comprising the step of placing a protective element proximate at least one of the cornea molding material and the iris button prior to molding the iris assembly.

19. A method for making an iris assembly for a prosthetic eye device, comprising the steps of:
   obtaining a photographic image of an iris portion of a natural eye with a digital camera and a plurality of flash elements;
   storing the obtained photographic image in a memory portion of a computer;
   adjusting the stored photographic image such that the image replicates the iris portion of the natural eye;
   printing the adjusted photographic image on archival paper using archival ink;
   curing the printed photographic image;
   trimming the cured photographic image to form an iris member;
   shaping the trimmed iris member to a convex shape;
   impregnating the shaped iris member with a mixture of methyl methacrylic monomer and polymer having a syrup-like viscosity;
   curing the impregnated iris member;
   assembling together a backside surface of the cured iris member to a frontside surface of an iris button with a mixture of methyl methacrylic monomer and polymer having a syrup-like viscosity therebetween, and placing a cornea molding material comprising a malleable mixture portion of methacrylic monomer and polymer having the consistency of modeling clay proximate a frontside surface of the cured iris member;
   molding together the cured iris member, iris button and cornea molding material to form a molded iris assembly;
   curing the molded iris assembly under a pressurized steam heat;
   allowing the cured iris assembly to cool; and
   cleaning and polishing the cooled iris assembly,
   wherein the cleaned and polished iris assembly yields an accurate reproduction of the iris portion of the natural eye.

20. The method of claim 19, further comprising the step of molding a projecting stem portion of the molded iris assembly.

21. The method of claim 20, further comprising the step of rotating the cooled iris assembly about the projecting stem portion to clean and polish the cooled iris assembly.

22. The method of claim 21, further comprising the step of removing the projecting stem portion from the cleaned and polished iris assembly.

23. The method of claim 19, further comprising the step of placing a protective element proximate at least one of the cornea molding material and the iris button prior to molding the iris assembly.

* * * * *